United States Patent

Takaishi et al.

Patent Number: 5,192,817
Date of Patent: Mar. 9, 1993

[54] PHENANTHRENE DERIVATIVES

[75] Inventors: Yoshihisa Takaishi, Tokushima; Kiyoto Goto, Naruto; Takuji Uesako, Tokushima; Toshiko Kuwahara, Tokushima; Masaaki Takai, Tokushima; Yukihisa Ono, Tokushima; Yoshihiro Taniguchi, Tokushima; Sachiko Manabe, Tokushima; Takahiro Asakuni, Kagawa, all of Japan

[73] Assignees: Otsuka Pharmaceutical Co., Ltd.; Otsuka Pharmaceutical Factory, Inc., both of Japan

[21] Appl. No.: 775,973

[22] PCT Filed: Mar. 5, 1991

[86] PCT No.: PCT/JP91/00289

§ 371 Date: Nov. 5, 1991

§ 102(e) Date: Nov. 5, 1991

[87] PCT Pub. No.: WO91/13855

PCT Pub. Date: Sep. 19, 1991

[30] Foreign Application Priority Data

Mar. 6, 1990 [JP] Japan ................................. 2-056184

[51] Int. Cl.$^5$ .................... C07C 49/215; C07C 50/32; C07D 307/77
[52] U.S. Cl. .................... 549/298; 560/255; 562/404; 568/326; 552/295; 552/298; 552/299
[58] Field of Search ............... 552/298, 299, 295; 549/457, 298; 560/239, 255; 562/5, 404; 568/326

[56] References Cited

FOREIGN PATENT DOCUMENTS 53-24069 7/1978 Japan.
59-39850 3/1984 Japan.

OTHER PUBLICATIONS

Chemical Abstracts, 101 (7) Aug., 13, 1984, p. 645, 55371f: Bull. Chem. Soc. Japan, 1984, 57 (3) pp. 747-751.
Chemical Abstracts, 108 (13) Mar. 28, 1988, p. 664, 112783h.
Chemical Abstracts, 107 (13) Sep. 28, 1987, p. 369, 112684k: Yaoxue Xuebao, 1987, 22 (5) pp. 377-379.

*Primary Examiner*—Howard T. Mars
*Assistant Examiner*—Kimberly J. Kestler
*Attorney, Agent, or Firm*—Finnegan, Henderson, Farabow, Garrett & Dunner

[57] ABSTRACT

Novel phenanthrene derivatives represented by the general formula (1),

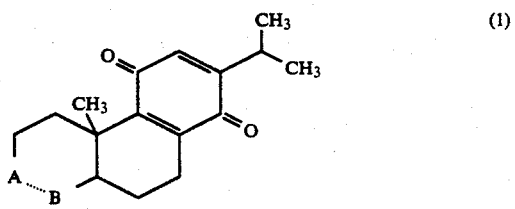

wherein the group of the formula

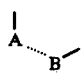

is a group of the formula

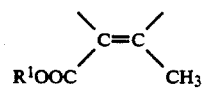

(wherein $R^1$ is a hydrogen atom or a lower alkyl group), a group of the formula

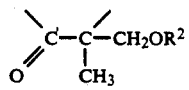

(wherein $R^2$ is a hydrogen atom or a lower alkanoyl group) or a group of the formula

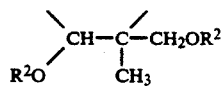

(wherein $R^2$ is the same as defined above), and salts thereof, and other compounds derived therefrom and salts thereof; processes for preparing the same; and interleukin-1 (IL-1) inhibitors containing the abovementioned novel phenanthrene derivatives as to the active ingredient(s).

8 Claims, No Drawings

PHENANTHRENE DERIVATIVES

FIELD OF THE INVENTION

The present invention relates to novel phenanthrene derivatives, salts thereof, production processes therefor, and interleukin-1 (IL-1) inhibitors containing the novel phenanthrene derivatives as active ingredients.

PRIOR ART

The phenanthrene derivatives of the present invention are novel compounds not disclosed in any literature.

In the Second International Lymphokine Workshop, it was decided that a standard name of interleukin-1 (IL-1) be given to all of the physiologically active substances which had been reported under various names such as Lymphocyte Activating Factor (LAF), Mitogenic Protein, Helper peak-1, T-cell replacing factor III (TRF-III), T-cell replacing factor macrophage (TRFM), B-cell activating factor, B-cell differentiation factor and the like [Cellular Immunol., 48. 433–436 (1979)]. The decision is based on the ground that each of the above physiologically active substances cannot be distinguished from others as a different substance and that each conventional name merely indicates a physiological activity viewed from a different angle.

The IL-1 is known as an important biologically active substance which induces and transfers systemic biological reactions such as infection and inflammation, and has by itself a strong antitumor activity [Hirai, Y. et al.: "Gann Monograph on Cancer Research", Japan Scientific Societies Press, Tokyo (1988)]. Also, the IL-1 has been confirmed to induce biological reactions which are seen in the human body during inflammation, such as pyrexia, increase in white blood cell count, activation of lymphocyte, induction of hepatic acute phase protein synthesis, and the like [Dinarello, C. A.: Interleukin-1; Rev. Infect. Dis., 6, 51-95 (1984), Kluger, M. J., Oppenheim, J. J. & Powanda, M. C.; The Physiologic, Metabolic and Immunologic Actions of interleukin-1; Alan R. Liss, Inc., New York (1985)].

The IL-1 has various biological activities and is thought to be a biologically active substance necessary for the maintenance of homeostatis of the human body. However, if the controlling function for IL-1 production becomes abnormal to give rise to accentuation of IL-1 production and resultant excessive production of IL-1, it would cause various diseases. In rheumatoid arthritis, for example, it is reported that there are strong relationships between production of IL-1 by synovium and degree of inflammation of arthricular synovial membrane, and between production of IL-1 by synovium and degree of joint changes and between production of IL-1 by synovium and degree of HLA-DR antigen expression in synovial membrane [Miyasaka, N., Sato, K., Goto, M., Sasano, M., Natsuyama, M., Inoue, K. and Nishioka, K.: Augmented interleukin-1 production and HLA-DR expression in the synovium of rheumatoid arthritis patient; Arthritis Rheum., 31, (4), 480–486, (1988)].

It is therefore considered that the inhibition of excessive IL-1 release from cells could block various physiological activities in which the IL-1 participates.

Currently, glucocorticoid hormone is in use as a treating agent for chronic inflammatory diseases, and part of the activities is known to lie in the inhibition of IL-1 production [Lew, W., Oppenheim, J. J. & Matsushima, K.; Analysis of the suppression of IL-1α and IL-1β production in human peripheral blood mononuclear adherent cells by a glucocorticoid hormone; J. Immunol., 140, (6), 1895-1902 (1988)]. However, the glucocorticoid is known to cause, as a disadvantage, various severe side-effects owing to multiple physiological activities.

Hence in the pharmaceutical industry, particularly in the field for treating chronic inflammatory diseases, there is now desired the development of a novel substance which has no side-effects as seen in glucocorticoid, which has excellent safety in other toxicities and side-effects, and which has high selectivity.

Compounds having structural formulas similar to those of the phenanthrene derivatives of the present application are disclosed in the following literatures (1)–(19):

(1) Chem. Abstr., 109 (23), 1988, 208280t: Planta Med., 1988, 54 (4), 330-332, (Eng.)
(2) Chem. Abstr., 108 (13), 1988, 112783n: Jiegou Huaxue, 1986, 5 (3), 172-5, (Eng.)
(3) Chem. Abstr., 96 (25), 1982, 214288f: Yaoxue Xuebao, 1982, 17 (2), 146-150, (Ch.)
(4) Chem. Abstr., 109 (7), 1988, 54996s: Yougi Huaxue, 1987, (6), 455-458, (Ch.)
(5) Chem. Abstr., 107 (13), 1987, 112684k: Yaoxue Xuebao, 1987, 22 (5), 377-379, (Ch.)
(6) Chem. Abstr., 104 (5), 1986, 31722g: Zhiwu Xuebao, 1985, 27 (5), 516-519, (Ch.)
(7) Chem. Abstr., 106 (13), 1987, 99342e: Helv. Chim. Acta, 1986, 69 (6), 1395-1417, (Ger.)
(8) Chem. Abstr., 93 (11), 1980, 114753y: Tetrahedron, 1979, 35 (22), 2693-2695, (Eng.)
(9) Chem. Abstr., 108 (15), 1988, 128494e: Phytochemistry, 1988, 27 (1), 221-224, (Eng.)
(10) Chem. Abstr., 107 (22), 1987, 205014g: Saengyak Hakheechi 1987, 18 (2), 99-102, (Korean)
(11) Chem Abstr., 96 (25), 1982, 218061z: J. Org. Chem., 1982, 47 (12), 2364-2369, (Eng.)
(12) Chem. Abstr., 108 (17), 1988, 147176u: Fitoterapia 1987, 58 (4), 285, (Eng.)
(13) Chem. Abstr., 97 (7), 1982, 56046q: Bull. Chem. Soc. Japan, 1982, 55 (4), 1168-1173, (Eng.)
(14) Chem. Abstr., 101 (7), 1984, 55371f: Bull. Chem. Soc. Japan, 1984, 57 (3), 747-751, (Eng.)
(15) Chem. Abstr., 101 (3), 1984, 20520b: Helv. Chim. Acta, 1984, 67 (1), 201-208, (Ger.)
(16) Chem. Abstr., 87 (15), 1977, 114548m: Helv. Chim. Acta, 1977, 60 (4), 1233-1238, (Ger.)
(17) CHem. Abstr., 87(9), 1977, 65321w: Helv. Chim. Acta, 1977, 60 (4), 1443-1447, (Ger.)
(18) Chem. Abstr., 84 (7), 1976, 44445a: Helv Chim. Acta, 1975, 58 (7), 1899-1912, (Ger.)
(19) Chem. Abstr., 80 (7), 1974, 37314h: Helv. Chim. Acta, 1973, 56 (7), 2534-2539, (Eng.)

The above literatures (1)–(19), although disclosing compounds having structural formulas similar to those of the phenanthrene derivatives of the present application, give no disclosure as to their pharmacological activities.

The following literature (20):
(20) Japanese Patent Application Kokai (Laid-Open) No. 39850/1984 discloses compounds having structural formulas similar to those of the phenanthrene derivatives of the present application and describes that these compounds have an antitumor activity and the same pharmacological activity as vitamin K, but gives no disclosure on inhibitory activity for IL-1.

Also, the following literature (21):

(21) Chem. Abstr., 88 (1), 1978, 7094j : Tetrahedron, 1977, 33 (12), 1457-67 (Eng.)

discloses compounds having the same basic skeletons as the phenanthrene derivatives of the present application but having different side chains and describes that these compounds have an inhibitory activity for mouse Lewis lung cancer and lymphocytic leukemia, but gives no disclosure on inhibitory activity for IL-1.

The following literature (22):

(22) Chem. Abstr., 107 (17), 1978, 151210x: Shanghai Yike Daxue Xuebao, 1986, 13 (4), 267-272 (Ch.)

discloses that triptonide and triptolide extracted from Triptergium Wilfordii Hook fil. var. Regelii Makino which is a material for extracting the phenanthrene derivatives of the present application, have an activity for hindering the propagation of lymphocytes induced by concanavalin A, but gives no disclosure on inhibitory activity for IL-1.

The following literatures (23), (24) and (25):

(23) Contraception, 1987, 36 (3), 335-345

(24) Chinese Medical Journal, 1981, 94 (12), 827-834

(25) Chinese Medical Journal, 1981, 94 (7), 405-412 disclose that the above-mentioned Triptergium Wilfordii *Hook fil.* var. Regelii *Makino* is effective as a treating agent for chronic rheumatic arthritis and various skin diseases and also as a sterilizing agent (literature 23) that the material is effective for treatment of systemic lupus erythematosus (a collagen disease) (literature 24), and that the material is effective for chronic rheumatoid arthritis and ankylosing spondylitis (literature 25), but gives no disclosure on inhibitory activity for IL-1.

DISCLOSURE OF THE INVENTION

An object of the present invention is to provide novel substances useful as IL-1 inhibitors satisfying the requirements in pharmaceutical industry.

The present invention relates to phenanthrene derivatives selected from the group consisting of compounds represented by the general formula (1)

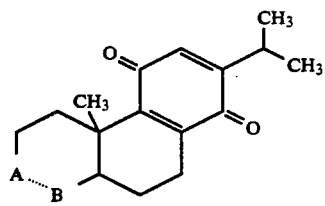

[wherein the group of the formula —A . . . B— is a group of the formula

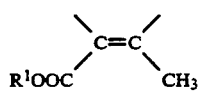

(wherein $R^1$ is a hydrogen atom or a lower alkyl group), or a group of the formula

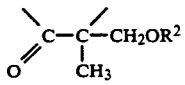

(wherein $R^2$ is a hydrogen atom or a lower alkanoyl group) or a group of the formula

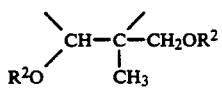

(wherein $R^2$ is the same as defined above) or a group of the formula

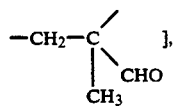

a compound of the formula (2),

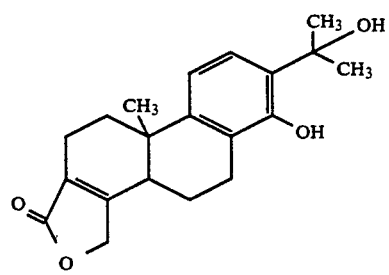

a compound of the formula (3),

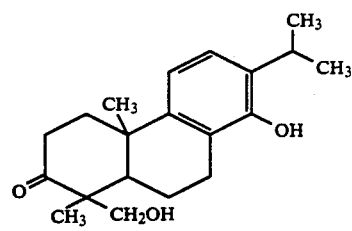

compounds represented by the general formula (4)

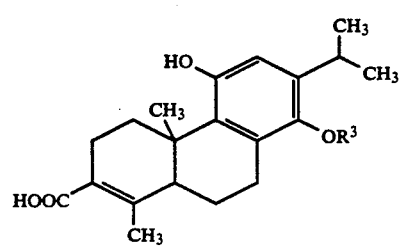

(wherein $R^3$ is a hydrogen atom of a methyl group), a compound of the formula (7),

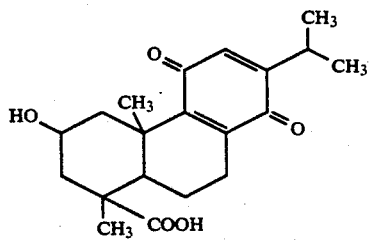

compounds represented by the general formula (8)

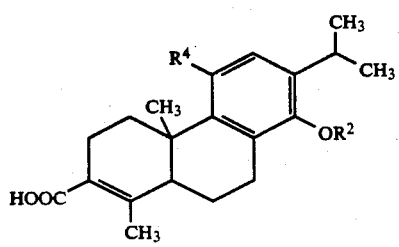

(wherein $R^2$ is the same as defined above and $R^4$ is a lower alkanoyloxy group),
and compounds represented by the general formula (9)

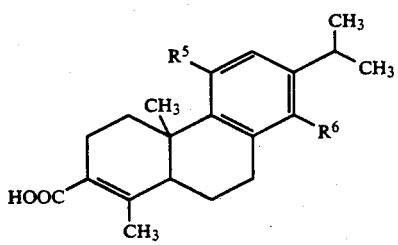

(wherein $R^5$ and $R^6$ are each a lower alkoxy group);
salts thereof; production processes therefor; and interleukin-1 (IL-1) inhibitors containing the novel phenanthrene derivatives as active ingredients.

In the present specification, as the lower alkyl group, there can be mentioned, for example, straight-chain or branched-chain alkyl groups of 1–6 carbon atoms, such as methyl, ethyl, propyl, isopropyl, butyl, tert-butyl, pentyl, hexyl and the like.

As the lower alkanoyl group, there can be mentioned, for example, straight chain or branched chain alkanoyl groups of 1–6 carbon atoms, such as formyl, acetyl, propionyl, butyryl, isobutyryl, pentanoyl, hexanoyl and the like.

As the lower alkanoyloxy group, there can be mentioned, for example, straight chain or branched chain alkanoyloxy groups of 2–6 carbon atoms, such as acetyloxy, propionyloxy, butyryloxy, isobutyryloxy, pentanoyloxy, hexanoyloxy and the like.

As the lower alkoxy group, there can be mentioned, for example, straight chain or branched chain alkoxy groups of 1–6 carbon atoms, such as methoxy, ethoxy, propoxy, isopropoxy, butoxy, tert-butoxy, pentyloxy, hexyloxy and the like.

The phenanthrene derivatives of the present invention can be produced by various processes, depending upon the types.

For example, each of the compound of the general formula (1) wherein the group $-A \ldots B-$ is a group

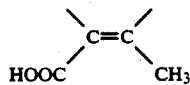

the compound of the general formula (1) wherein the group $-A \ldots B-$ is

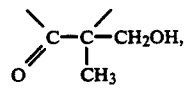

the compounds of the general formula (1) wherein the group $-A \ldots B-$ is

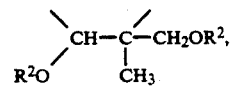

the compound of the general formula (1) wherein the group $-A \ldots B-$ is

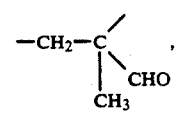

the compound of the formula (2), the compound of the formula (3), the compound of the formula (7) and the compound of the general formula (4) wherein $R^3$ is a methyl group, can be extracted and isolated from Tripterygium Wilfordii Hook fil. var. Regelii Makino (a plant of Celastraceae).

This extraction and isolation operation can be conducted according to the one ordinarily applied to general plant components. The above operation is effected specifically by a method of first subjecting Tripterygium Wilfordii Hook fil. var. Regelii Makino to extraction with an ordinary polar solvent such as methanol, ethanol or the like, concentrating the resulting extract under reduced pressure to obtain a primary extract, and collecting an intended compound from the primary extract using various methods utilizing the physical and chemical properties of the intended compound. As the methods used for collecting the intended compound, there can be employed ordinary methods, for example, (1) a method of utilizing the difference in solubility between intended compound and impurities, (2) a method of utilizing the difference in adsorptive affinity with appropriate absorbents, such as active carbon, ion exchange resin such as Amberlite or the like, or silica gel, Sephadex or the like, (3) a method of utilizing the difference in partition law between two liquid phases, and combinations of these methods. Preferable of the above collection methods is, for example, a method of suspending the above-mentioned primary extract in water, subjecting the suspension to extraction with ethyl acetate, subjecting the extract to silica gel column chromatography, effecting elution with an appropriate solvent such as ethyl acetate-n-hexane mixture, methanol-chloroform mixture or the like, subjecting the eluate to appropriate combinations of various column chromatographies such as silica gel column chromatography, Sephadex LH 20 column chromatography, gel filtration column chromatography, high performance liquid chromatography and the like, and effecting elution with appropriate solvents such as ethyl acetate-n-hexane mixture, methanol-chloform mixture, acetone-chloroform mixture and the like. Thus, the intended compound of the present invention can be purified and isolated.

The present compounds other than mentioned above can be produced by using the above-mentioned present compounds obtained from Tripterygium Wilfordii Hook fil. var. Regelii Makino, as a material and subjecting them to the following chemical treatments.

That is, the compound of the general formula (1) wherein the group —A . . . B— is a group

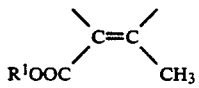

and $R^1$ is a lower alkyl group [said compound is hereinafter referred to as "compound (1a)"], can be produced by reacting a compound corresponding to the compound (1a), obtained by changing the $R^1$ of the compound (1a) to a hydrogen atom [said compound is hereinafter referred to as "compound (1b)"], with an alcohol in an appropriate inert solvent in the presence of an acid catalyst. As the inert solvent, there can be mentioned various solvents which give no adverse effect on the reaction, for example, ethers such as diethyl ether, tetrahydrofuran, dioxane and the like, halogenated hydrocarbons such as dichloromethane, dichloroethane, chloroform and the like, aromatic hydrocarbons such as benzene, toluene, xylene and the like, alcohols such as methanol, ethanol, propanol and the like, and mixtures thereof. As the acid catalyst, there can be used, for example, Lewis acids such as aluminum chloride, stannic chloride, titanium tetrachloride, boron trichloride, boron trifluorideethyl ether complex, zinc chloride and the like, inorganic acids such as hydrochloric acid, nitric acid, sulfuric acid and the like, organic acids such as trichloroacetic acid, trifluoroacetic acid, methanesulfonic acid, acetic acid and the like, and acid type ion exchange resins. As the alcohol to be reacted with the compound (1b), there can be used methanol, ethanol, propanol, etc., and these alcohols function also as a solvent. The desirable proportion of the alcohol to the compound (1b) is generally at least equimolar, preferably about 1-30 moles per 1 mole of the compound (1b). The reaction is generally conducted at room temperature to a temperature about equal to the refluxing temperature of the solvent, in about 1-72 hours, preferably about 3-24 hours.

The compound (1a) can also be produced by the following diazotization method. That is, in the method, the compound (1b) is reacted, in the presence of an inert solvent, with a diazo compound corresponding to the ester residue in esterified carboxyl group, such as diazomethane, phenyldiazomethane, diphenyldiazomethane or the like. As the inert solvent, there can be mentioned, for example, halogenated hydrocarbons such as dichloromethane, dichloroethane, chloroform, carbon tetrachloride and the like, ethers such as dioxane, tetrahydrofuran, diethyl ether, dimethyl ether and the like, nitro compounds such as nitromethane, nitrobenzene and the like, alcohols such as methanol, ethanol and the like, esters such as ethyl acetate, methyl acetate and the like, aliphatic hydrocarbons such as hexane, heptane, octane and the like, nonpolar solvents such as dimethylformamide, dimethyl sulfoxide, hexamethylphosphoric triamide and the like, and carbon disulfide. The desirable proportion of the diazo compound to the compound (1b) is at least equimolar, preferably about 1-3 moles per 1 mole of the compound (1b). The reaction proceeds favorably at $-10°$ C. to room temperature and is complete generally in about 10 minutes to about 6 hours.

The compound of the general formula (1) wherein the group —A . . . B— is a group

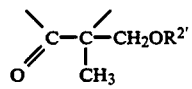

and $R^{2'}$ is a lower alkanoyl group [i.e. the compound (1d)] or the compound of the general formula (1) wherein the group —A . . . B— is a group

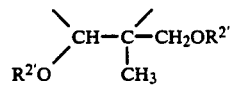

and $R^{2'}$ is a lower alkanoyl group, can be produced by reacting a compound (1c) corresponding to the above compound, obtained by changing the $R^{2'}$ or the above compound to a hydrogen atom, with a compound represented by the general formula $$(R^{2'})_2O \qquad (5)$$

or the general formula $$R^{2'}X \qquad (6)$$

[wherein $R^{2'}$ is a lower alkanoyl group and X is a halogen atom].

The above alkanoylation reaction is conducted in the presence or absence of a basic compound. As the basic compound, there can be mentioned, for example hydroxides, carbonates and bicarbonates of alkali metals, as well as organic bases such as pyridine, piperidine and the like. The reaction proceeds in the presence or absence of a solvent. As the solvent, there can be mentioned, for example, ketones such as acetone, methyl ethyl ketone and the like, ethers such as diethyl ether, dioxane and the like, aromatic hydrocarbons such as benzene, toluene, xylene and the like, water and pyridine. The compound of the general formula (5) or (6) can be used in at least about equimolar amount, and is generally used in an equimolar amount to a large excess relative to the material compound. The reaction proceeds at 0°–200° C., and is generally conducted at about 0°–150° C. The reaction time is generally about 0.5–20 hours.

The compound of the general formula (4) wherein $R^3$ is a hydrogen atom, can be produced by reducing the compound (1b).

The reducing reaction of the compound (1b) is conducted by effecting catalytic reduction in the presence of a catalyst in an appropriate solvent. As the solvent, there can be mentioned, for example, water, acetic acid, alcohols such as methanol, ethanol, isopropyl alcohol and the like, hydrocarbons such as hexane, cyclohexane and the like, ethers such as diethylene glycol dimethyl ether, dioxane, tetrahydrofuran, diethyl ether and the like, esters such as ethyl acetate, methyl acetate and the like, polar solvents such as dimethylformamide and the like, and mixtures thereof. As the catalyst, there can be mentioned palladium, palladium black, palladium-carbon, platinum, platinum oxide, copper chromite, Raney nickel, etc. The desirable amount of the catalyst used is generally about 0.02-1 times the compound (1b). The reaction is conducted under a hydrogen pressure of about 1-10 atm, and generally at about $-20°$ to $100°$ C., preferably at about $0°-70°$ C. in about 0.5-20 hours.

The reducing reaction of the compound (1b) can also be conducted by adding, to the compound (1b), an aqueous solution containing sodium hydrosulfite in an amount of 2-50 moles per 1 mole of the compound (1b), in the solvent mentioned in the above reduction reaction.

The compound of the general formula (8) can be obtained by reacting a compound of the general formula (4) wherein $R^3$ is a hydrogen atom, with a compound of the general formula (5) or (6). The reaction can be conducted under the same conditions as used in reacting a compound of the general formula (1) wherein the group $-A \ldots B-$ is a group

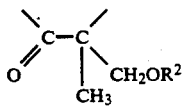

and $R^2$ is a hydrogen atom, with a compound of the general formula (5) or (6).

The compound of the general formula (9) can be obtained by reacting a compound of the general formula (4) wherein $R^3$ is a hydrogen atom, with an alkylating agent. The alkylation reaction is conducted in an appropriate solvent in the presence or absence of a basic compound. As the alkylating agent, there can be mentioned diazomethane, trimethylsilyl-diazomethane, alkyl halides such as methyl iodide and the like, lower alkylsulfonic acid esters such as $FSO_3CH_3$, $CF_3SO_3CH_3$, $(CH_3)_2SO_4$ and the like, lower alkyl oxonium halide chelate salts such as $(CH_3)_3O^+BF_4^-$, $(C_2H_5)_3O^+BF_4^-$ and the like, and lower alkoxy oxonium halide chelate salts such as $(C_2H_5O)_3O^+BF_4^-$ and the like. As the solvent, there can be mentioned, for example, water; lower alcohols such as methanol, ethanol, propanol and the like; ethers such as dioxane, tetrahydrofuran, diethyl ether, ethylene glycol monomethyl ether and the like; halogenated hydrocarbons such as dichloromethane, chloroform, carbon tetrachloride and the like; dimethylformamide; and mixtures thereof.

As the basic compound, there can be mentioned, for example, carbonates such as sodium carbonate, potassium carbonate, sodium hydrogencarbonate, potassium hydrogencarbonate and the like, and metal hydroxides such as sodium hydroxide, potassium hydroxide and the like.

The desirable amount of the alkylating agent, when it is diazomethane, is generally a large excess, preferably about 10-20 equivalents relative to the staring material compound. The desirable amount, when other alkylating agent is used, is at least equimolar, preferably 1-10 moles per 1 mole of the material compounds. The reaction is conducted generally at about $-30°$ C. to about $100°$ C., preferably at about $-20°$ C. to about $70°$ C., and is complete generally in about 0.5-20 hours.

Of the thus obtained phenanthrene derivatives of the present invention, those compounds having an acidic group, i.e. a phenolic hydroxyl group and (or) a carboxyl group can easily form respective salts by reacting with a basic compound. The present invention includes such salts. Specific examples of the basic compound used in production of the salts are hydroxides, carbonates and hydrides of alkali metals or alkaline earth metals, such as sodium hydroxide, potassium hydroxide, calcium hydroxide, sodium carbonate, potassium carbonate, sodium hydrogencarbonate, sodium hydride and the like. As the basic compound for salt formation, there can also be used organic amines such as methylamine, ethylamine, isopropylamine, morpholine, piperazine, piperidine, 3,4-dimethoxyphenethylamine and the like.

The salt formation reaction by the basic compound can be effected in an appropriate solvent according to the ordinary salt formation reaction. As the solvent, there can be mentioned, for example, water; lower alcohols such as methanol, ethanol, propanol and the like; ethers such as dioxane, tetrahydrofuran and the like; acetone; benzene; ethyl acetate; dimethyl sulfoxide; dimethylformamide; methylene chloride; and chloroform. The reaction is effected generally in air or under an oxygen-free condition, preferably in an inert gas atmosphere such as nitrogen, argon or the like, under a temperature condition of room temperature to about $100°$ C., preferably room temperature to about $50°$ C., in about 5 minutes to about 6 hours. The amount of the basic compound used is not particularly restricted, but desirably is generally 1 equivalent or more, preferably about 1-2 equivalents relative to the starting material. Thus, an intended salt can be obtained.

The phenanthrene derivatives and salts thereof according to the present invention, obtained by the above chemical treatments can be isolated and purified according to ordinary separation means, after the respective reactions. As the separation means, there can be appropriately employed, for example, solvent removal by distillation, solvent extraction, precipitation, recrystallization, column chromatography, and preparative chromatography.

The compounds of the present invention include also stereoisomers and optically active compounds.

The thus obtained phenanthrene derivatives and salts thereof according to the present invention have an inhibitory activity for IL-1 and are useful as an IL-1 inhibitor.

The compounds of the present invention can be administered to human and other animals as it is or in a form of a usual pharmaceutical composition prepared by using ordinary pharmaceutical carriers.

The carriers, pharmaceutical composition form (unit form for administration), preparation thereof, administration route thereof, etc. can be the same as employed in ordinary pharmaceutical compositions. That is, the pharmaceutical compositions include tablets, pills, powder, solutions, suspensions, emulsions, granules, capsules, suppositories, injections (solutions, suspensions, etc.), etc, all containing an effective amount of the present compound(2). These pharmaceutical compositions of various forms can be prepared according to ordinary methods, and the carriers used therein can be prepared according to ordinary methods, and the carriers used therein can be various ones of conventional use. For example, tablets are prepared by mixing present compound(s) as active ingredient(s) with excipient(s) such as gelatin, starch, lactose, magnesium stearate, talc, gum arabic and the like and then shaping the mixture. Capsules are prepared by mixing the active ingredient(s) with an inert filler or diluent and filling the mixture into hard gelatin capsules, soft capsules, or the like. Parenteral administration agents such as injection and the like are prepared by dissolving or suspending present compound(s) as active ingredient(s) in a sterilized liquid carrier; the liquid carrier used in this case is water and a physiological saline solution; the injection or the like prepared thus may further contain an ordinary solubilizing agent, a buffer agent, an analgesic agent, etc. Further, the above pharmaceutical compositions of various forms can contain, if necessary, a coloring agent, a preservative, a perfume, a seasoning agent, a sweetening agent, etc. and other pharmaceutical compounds.

The amount of the phenanthrene derivative(s) and salt(s) thereof according to the present invention, to be included as active ingredient(s) in each of the above pharmaceutical compositions is not particularly restricted and can be appropriately selected from a wide range, but desirably is generally about 1–70% by weight, preferably about 1–30% by weight.

The administration method of the pharmaceutical compositions prepared above has no particular restriction. For example, the tablets, pills, powder, granules, capsules, etc. are administered orally; the injection (solution, suspension, etc.) is administered intravenously as it is or after mixing it with an ordinary auxiliary solution such as grape sugar, amino acid or the like, or, as necessary, administered intramuscularly, intracutaneously, subcutaneously or intraperitoneally as it is.

The administration dosages of the above pharmaceutical compositions are appropriately selected depending upon the usage, the age, sex and other conditions of patient, the degree of disease, etc. However, the administration is generally made so that the present compound(s) as active ingredient(s) is (are) administered in an amount of about 0.1–1,000 mg per kg (body weight) per day. The pharmaceutical compositions can be administered in 1–4 times per day. Each unit form for administration desirably contains about 1–600 mg of the active ingredient(s).

EXAMPLES

In order to describe the present invention in more detail, below are given Examples on production processes for phenanthrene derivatives of the present invention, as well as results on pharmacological tests conducted for compounds of the present invention.

EXAMPLE 1

108 Kilograms of stalks of Tripterygium Wilfordii Hook fil. var. Regelii Makino was cut into small pieces and subjected to extraction with 200 liters of methanol at room temperature for 7 days. The extract was concentrated under reduced pressure to obtain a crude extract. The crude extract was suspended in 20 liters of water, and the suspension was subjected to extraction with three 20 liters portions of ethyl acetate. The ethyl acetate layers were combined and concentrated under reduced pressure to obtain 1,300 g of an ethyl acetate extract.

1,200 Grams of the ethyl acetate extract was subjected to silica gel column chromatography [1,500 g of Merck Silica Gel 60, having 70–230 meshes, manufactured by Merck & Co., Inc. (hereinafter referred to as "Merck")], extracted with 10 liters each of 20%, 40%, 60% and 80% ethyl acetate/n-hexane (v/v) and 10 liters of ethyl acetate in this order, and was further extracted with 10 liters each of 10%, 20% and 30% methanol/ethyl acetate (v/v) and 10 liters of methanol in this order, to collect 500 ml each of fractions (1) to (11).

Of these fractions, the fraction (4) was subjected to evaporation under reduced pressure to remove the solvent. Of 57 g of the resulting residue, 53 g was subjected to silica gel chromatography (1,200 g of Merck Silica Gel 60, having 70–230 meshes, a product of Merck). Fractionation and elution were made with 10 liters of chloroform and 10 liters of 5% methanol/chloroform (v/v) to obtain fractions (4-1) to (4-7). The fractions (4-5, 6) were combined and concentrated under reduced pressure to obtain 19.96 g of a residue. The residue was subjected four times to column chromatography using 2,000 ml of Sephadex LH-20 [a product of Pharmacia LKB Biotechnology Inc.]. Fractionation and elution were made with 3,000 ml of methanol to effect purification. Then, recrystallized from methanol to obtain 2.654 g of 3,4,4a,5,8,9,10,10a-octahydro-1,4a-dimethyl-7-(1-methylethyl)-5,8-dioxo-2-phenanthrenecarboxylic acid as light yellow needles.

Molecular formula: $C_{20}H_{24}O_4$ (Mw: 328).

$[\alpha]_D^{25} = +296°$ (c=0.14, chloroform).

Rf$_1$: 0.36 [5% methanol/chloroform (v/v)].

Rf$_2$: 0.16 [40% ethyl acetate/n-hexane (v/v)].

IR$\nu_{max}$ KBr) cm$^{-1}$: 2970, 1710, 1680, 1650, 1605, 1298, 1266, 1100, 911, 735, UV$\lambda_{max}$ (CH$_3$OH) nm: 231 (e=10030), 260 ($\epsilon$=15040)

$^1$H NMR (400 MHz, Chloroform-d$_1$) δ ppm: 1.12 (6H, d, J=6.8 Hz), 1.18 (3H, s), 1.14–1.56 (2H, m), 2.12 (3H, s), 2.22–2.26 (2H, m), 2.39 (1H, ddd, J=20.5, 11.2, 6.8 Hz), 2.42–2.63 (2H, m), 2.76–2.82 (1H, m), 2.79 (1H, dd, J=20.5, 6.4 Hz), 3.01 (1H, sept d, J=6.8, 1.0 Hz), 6.38 (1H, d, J=1.0 Hz).

$^{13}$C NMR (67.5 MHz, chloroform-d$_1$) δppm: 18.4 (q), 18.6 (t), 19.1 (q), 21, 3×2 (q), 24.5 (t), 25.1 (t), 26.3 (d), 31.8 (t), 36.5 (s), 47.3 (d), 124.5 (s), 131.7 (d), 142.4 (s), 148.1 (s), 148.6 (s), 153.1 (s), 174.5 (s), 187.5 (s), 187.8 (s).

EI-MS m/z (relative intensity): 328 [M]+(100), 313 [M-CH3]+(26), 310 (68), 295 (32), 282 (23), 267 (32), 229 (41), 204 (46), 191 (29), 189 (24).

HR-MS m/z: 328.1662 [M]+, $C_{20}H_{24}O_4$ 328.1675 (calculated).

EXAMPLE 2

The fraction (5) obtained in Example 1 was subjected to evaporation under reduced pressure to remove the solvent. Of 60 g of the resulting residue, 55 g was subjected to silica gel column chromatography (1000 g of Merck Silica Gel 60, having 70–230 meshes). Elution was made with 8 liters of chloroform and 4 liters of 5% methanol/chloroform (v/v) to obtain fractions (5-1 to 5-10). The fraction (5-1) is concentrated under reduced pressure to obtain 3.41 g of a residue. Then the residue was subjected to silica gel column chromatography (300 g of Merck Silica Gel 60, 230–400 meshes). Then fractionation and elution were made with 1 liter of 25% ethyl acetate/n-hexane (v/v), 500 ml of 30% ethyl acetate/n-hexane (v/v) and 200 ml of 50% ethyl acetate/n-hexane (v/v) to obtain fractions (5-1-1 to 5-1-7).

The fraction (5-1-3) was concentrated under reduced pressure to obtain 1.533 g of 5,6,8,8a,9,10-hexahydro-8-hydroxymethyl-4b,8-dimethyl-2-(1-methylethyl)-1,4,7(4bH)-phenanthrenetrione as a yellowish orange powder.

Molecular formula: $C_{20}H_{26}O_4$ (Mw: 330).
$[\alpha]_D^{25} = +336°$ (c=0.21, chloroform).
$Rf_1$: 0.61 [5% methanol/chloroform (v/v)].
$Rf_2$: 0.19 [40% ethyl acetate/n-hexane (v/v)].
$IR\nu_{max}$ (KBr) cm$^{-1}$: 3440, 1705, 1650, 1465, 1300, 1235, 1040.
$UV\lambda_{max}$ (CH$_3$OH) nm: 258 ($\epsilon$=14021).
$^1$H NMR (400 MHz, chloroform-d$_1$) $\delta$ppm: 1.11 (6H, d, J=6.8 Hz), 1.28 (3H, s), 1.35 (3H, s), 1.45 (1H, dddd, J=13.7, 13.7, 13.7, 5.4 Hz), 1.83 (1H, ddd, J=13.7, 10.3, 5.9 Hz), 1.88 (1H, ddt, J=13.2, 6.8, 2.0 Hz), 2.01 (1H, dd, J=13.2, 2.4 Hz), 2.29 (1H, ddd, J=20.0, 11.7, 6.8 Hz), 2.48 (1H, ddd, J=15.6, 8.8, 5.9 Hz), 2.69 (1H, ddd, J=16.1, 10.7, 5.9 Hz), 2.79–2.89 (2H, m), 3.00 (1H, sept d, J=6.8, 1.5 Hz), 3.46, 4.05 (each 1H, ABq, J=11.2 Hz), 6.37 (1H, s).
$^{13}$NMR (67.5 MHz, chloroform-d$_1$) $\delta$ppm: 17.8 (t), 20.9 (q), 21.2×2 (q), 22.9 (q), 25.4 (t), 26.3 (d), 34.1 (t), 34.3 (t), 37.0 (s), 50.4 (s), 51.6 (d), 65.3 (t), 131.7 (d), 142.4 (s), 147.8 (s), 153.2 (s), 187.2 (s), 187.4 (s), 220.0 (s).
EI-MS m/z (relative intensity): 330 [M]+(100), 315 [M-CH$_3$]+(16), 312 [M-H$_2$O]+(24), 300 (50), 299 (34), 285 (27), 269 (29), 229 (35), 215 (26), 175 (25).
HR-MS m/z: 330.1854 [M]+, $C_{20}H_{28}O_4$ 330.1831 (calculated).

EXAMPLE 3

The fraction (5-2) obtained in Example 2 was concentrated under reduced pressure to obtain 38.2 g of a residue. The residue was subjected to silica gel column chromatography (1000 g of Merch Silica Gel 60), then eluted with 4 liters of chloroform, 3 liters of 2% methanol/chloroform (v/v) and 3 liters of 5% methanol/chloroform (v/v) to obtain fractions (5-2-1 to 5-2-6). The fraction (5-2-2) was concentrated under reduced pressure to obtain 3.278 g of a residue. The residue was subjected to Sephadex LH-20 column chromatography, (500 ml), then eluted with 1 liter of methanol to obtain fractions (5-2-2-1 to 5-2-2-3). The fraction (5-2-2-1) was concentrated under reduced pressure to obtain 0.916 g of a residue. The residue was subjected to silica gel column chromatography (100 g of Merck Silica Gel 60, having 230–400 meshes), then eluted with 2 liters of 2% methanol/chloroform (v/v). The eluate was subjected to silica gel column chromatography (300 g of Merck silica gel 60, having 230–400 meshes). Fractionation and elution were made with 1 liter of 2% methanol/chloroform (v/v) to obtain 97 mg of 1,2,3,4,4a,5,8,9,10,10a-decahydro-2-hydroxy-1-(hydroxymethyl)-1,4a-dimethyl-7(1-methylethyl)-5,8-dioxo-phenanthrene as an amorphous substance.

Molecular formula: $C_{20}H_{28}O_4$ (MW: 332)
$[\alpha]_D^{25} = +31.3°$ (c=0.38, chloroform).
$Rf_1$: 0.37 [5% methanol/chloroform (v/v)].
$Rf_2$: 0.10 [40% ethyl acetate/n-hexane (v/v)].
$IR\nu_{max}$ (KBr) cm$^{-1}$: 3369, 2971, 1710, 1646, 1596, 1290, 1265, 1080, 906, 755.
$UV\lambda_{max}$ (CH$_3$OH) nm: 260 ($\epsilon$=11840).
$^1$H NMR (400 MHz, chloroform-d$_1$) $\delta$ppm: 1.09 (3H, d, J=6.8 Hz), 1.10 (3H, d, J=6.8 Hz), 1.19 (1H, brd, J=11.7 Hz), 1.23 (3H, s), 1.25 (1H, m), 1.29 (3H, s), 1.38 (1H, dddd, J=19.0, 11.7, 11.7, 4.9 Hz), 1.81 (1H, ddd, J=13.7, 8.3, 3.9 Hz), 1.91–2.01 (2H, m), 2.31 (1H, ddd, J=20.5, 11.7, 7.3 Hz), 2.73 (1H, dd, J=20.5, 4.9 Hz), 2.81 (1H, ddd, J=13.7, 3.9, 3.9 Hz), 2.98 (1H, sept d, J=6.8, 1.0 Hz), 3.35 (1H, d, J=11.2 Hz), 3.48 (1H, dd, J=11.7, 4.9 Hz), 4.26 (1H, d, J=11.2 Hz), 6.32 (1H, d, J=1.0 Hz).
$^{13}$C NMR (67.5 MHz, chloroform-d$_1$) $\delta$ppm: 17.4 (t), 20.9 (q), 21.3×2 (q), 22.8 (q), 26.3 (d), 26.4 (t), 28.1 (t), 34.2 (t), 37.8 (s), 43.1 (s), 51.8 (d), 64.0 (t), 80.0 (d), 131.9 (d), 142.7 (s), 149.6 (s), 153.1 (s), 187.7 (s), 187.8 (s).
EI-MS m/z (relative intensity): 332 [M]+(19), 314 [M-H$_2$O]+(80), 299 (23), 296 [M-2H$_2$O]+(20), 281 (58), 203 (59), 91 (66), 43 (100).
HR-MS m/z: 332.1939 [M]+, $C_{20}H_{28}O_4$ 332.1988 (calculated).

EXAMPLE 4

There are combined the fractions (5-2-1) and (5-2-2-2) obtained in Example 3 and the mother liquor for 3,4,4a,5,8,9,10,10a-octahydro-1,4a-dimethyl-7-(1-methylethyl)-5,8-dioxo-2-phenanthrenecarboxylic acid obtained in Example 1. The mixture is concentrated under reduced pressure to obtain 3.433 g of a residue. The residue was subjected to fractionation and purification by using 300 ml of Toyo Pearl WH-40F column chromatography [(a product of Tosoh Corporation), eluted with 500 ml of 50% methanol/chloroform (v/v)], 1800 ml of Toyo Pearl WH-40F column chromatography, [eluted, with 2 liters of 50% methanol/chloroform (v/v)] and silica gel column chromatography [100 g of Merck Silica Gel 60, eluted with 1 liter of 33% ethyl acetate/n-hexane (v/v)] in this order to obtain 97 mg of 3,4,4a,9,10,10a-hexahydro-8-hydroxy-1-(hydroxymethyl)-1,4a-dimethyl-7-(1-methylethyl)-2(1H)-phenanthrene and 70 mg of crude 3b,4,5,9b,10,11-hexahydro-6-hydroxy-7-(1-hydroxy-1-methylethyl)-9b-methylphenanthro[1,2-C]-furan-(1(3H)-one each as an amorphous substance. The crude 3b,4,5,9b,10,11-hexahydro-6-hydroxy-7-(1-hydroxy-1-methylethyl)-9b-methylphenanthro[1,2-c]-furan-1(3H)-one is recrystallized from methanol to obtain 40 mg of a purified substance as colorless granular crystals.

3,4,4a,9,10,10a-Hexahydro-8-hydroxy-1-(hydroxymethyl)-1,4a-dimethyl-7-(1-methylethyl)-2(1H)-phenanthrenone Molecular formula: $C_{20}H_{28}O_3$ (Mw: 316).
$[\alpha]_D^{25} = +89.3°$ (c=1.06, chloroform).
$Rf_1$: 0.44 [5% methanol/chloroform (v/v)].
$Rf_2$: 0.13 [40% ethyl acetate/n-hexane (v/v)].
$IR\nu_{max}$ (KBr) cm$^{-1}$: 3412, 2962, 1700, 1492, 1461, 1422, 1219, 1038, 757.
$UV\lambda_{max}$ (CH$_3$OH) nm: 271 ($\epsilon$=8620), 268 ($\epsilon$=2680) 340 ($\epsilon$=880).
$^1$H NMR (400 MHz, chloroform-d$_1$) $\delta$ppm: 1.23 (3H, d, J=6.8 Hz), 1.25 (3H, d, J=6.8 Hz), 1.28 (3H, s), 1.34 (3H, s), 1.70 (1H, ddd, J=13.2, 12.7, 12.7, 6.4 Hz), 1.98 (1H, m), 2.01 (1H, dd, J=18.1, 8.8 Hz), 2.10 (1H, dd, J=13.2, 2.4 Hz), 2.48 (1H, ddd, J=18.1, 7.8, 4.4 Hz), 2.57 (1H, m), 2.63 (1H, dd, J=15.1, 7.8 Hz), 2.69 (1H, ddd, J=15.1, 8.8, 4.4 Hz), 2.92 (1H, dd, J=16.6, 6.4 Hz), 3.12 (1H, sept, J=6.8 Hz), 3.54 (1H, d, J=11.2 Hz), 4.08 (1H, d, J=11.2 Hz), 6.80, 7.40 (each 1H, ABq, J=8.3 Hz).
EI-MS m/z (relative intensity): 316 [M]+(100), 301 [M-CH$_3$]+(60), 285 (31), 283 (31), 271 (90), 241 (42), 199 (51), 147 (51).
HR-MS m/z: 316.2006 [M]+, $C_{20}H_{28}O_3$ 316.2038 (calculated).

3b,4,5,9b,10,11-Hexahydro-6-hydroxy-7-(1-hydroxy-1-methylethyl)-9b-methylphenanthro[1,1-C]furan-1(3H)-one Molecular formula: $C_{20}H_{24}O_4$ (Mw: 328).
$Rf_1$: 0.50 [5% methanol/chloroform (v/v)].
$Rf_2$: 0.18 [40% ethyl acetate/n-hexane (v/v)].
$IR\nu_{max}$ (KBr) $cm^{-1}$: 3349, 3200, 2933, 1729, 1671, 1569, 1401, 1380, 1267, 1077, 1033, 755.
$UV\lambda_{max}$ ($CH_3OH$) nm: 220 ($\epsilon=15840$), 274 ($\epsilon=1950$) 283 ($\epsilon=2040$).
$^1H$ NMR (400 MHz, chloroform-$d_1$) δppm: 1.03 (3H, s), 1.63 (3H, s), 1.69 (3H, s), 1.68 (3H, m), 1.88 (1H, dddd, J=13.2, 13.2, 10.7, 7.3 Hz), 1.98 (1H, ddd, J=13.2, 8.8, 3.6 Hz), 2.39 (1H, ddd, J=14.2, 6.8, 3.9 Hz), 2.48–2.52 (2H, m), 2.69 (1H, brd, J=13.2 Hz), 2.84 (1H, ddd, J=18.6, 10.7, 8.8 Hz), 2.98 (1H, dd, J=18.6, 7.3 Hz), 4.77, 4.83 (each 1H, ABq, J=7.1 Hz), 6.85 (1H, d, J=8.3 Hz), 6.96 (1H, d, J=8.3 Hz), 9.20 (1H, s).
$^{13}C$ NMR (67.5 MHz, chloroform-$d_1$) δppm: 18.2 (t), 19.7 (t), 22.3 (q), 22.5 (t), 30.3 (q), 30.4 (q), 32.6 (t), 36.3 (s), 41.01 (d), 70.6 (d), 76.1 (s), 114.8 (d), 122.6 (d), 123.3 (s), 125.0 (s), 127.8 (s), 145.9 (s), 153.6 (s), 163.2 (s), 174.3 (s).
EI-MS m/z (relative intensity): 328 [M]+(3), 310 [M-H20]+(100), 295 (73), 277 (2), 185 (10), 147 (18), 115 (8).
HR-MS m/z: 328.1629 [M]+, $C_{20}H_{24}O_4$ 328.1675 (calculated).

EXAMPLE 5

The fraction (5-2-6) obtained in Example 3 was concentrated under reduced pressure to obtain 1.782 g of a residue. The residue was subjected to silica gel column chromatography (400 g of Merck Silica Gel 60, having 230–400 meshes), then eluted with 1 liter of 5% methanol/chloroform (v/v) to effect fractionation and purification to obtain 0.124 g of 3,4,4a,9,10,10a-hexahydro-5-hydroxy-8-methoxy-1,4-a-dimethyl-7-(1-methylethyl)-2-phenanthrenecarboxylic acid as an amorphous substance.

Molecular formula: $C_{21}H_{28}O_4$ (Mw: 344).
$[\alpha]_D^{25} = +171.2°$ (c=1.0, chloroform).
$Rf_1$: 0.19 [5% methanol/chloroform (v/v)].
$Rf_2$: 0.16 [40% ethyl acetate/n-hexane (v/v)].
$IR\nu_{max}$ (KBr) $cm^{-1}$: 3400, 2963, 2620, 1681, 1620, 1412, 1262, 1224, 1032, 798, 758.
$UV\lambda_{max}$ ($CH_3OH$) nm: 222 ($\epsilon=9460$), 280 ($\epsilon=2180$) 287 ($\epsilon=2200$).
$^1H$ NMR (400 MHz, chloroform-$d_1$) δppm: 1.17 (3H, d, J=6.8 Hz), 1.18 (3H, s), 1.19 (3H, d, J=6.8 Hz), 1.59 (1H, m), 1.64 (1H, m), 2.18 (3H, brs), 2.21 (1H, dd, J=9.2, 6.4 Hz), 2.38 (1H, brd, J=12.4 Hz), 2.41 (1H, m, 2.63 (1H, m), 2.68 (1H, m), 3.03 (1H, ddd, J=13.2, 7.6, 3.6 Hz), 3.10 (1H, dd, J=16.8, 3.2 Hz), 3.25 (1H, sept, J=6.8 Hz), 3.69 (3H, s), 6.40 (1H, s).
$^{13}C$ NMR (100 MHz, chloroform-$d_1$) δppm: 18.6 (q), 18.7 (q), 19.9 (t), 23.8 (q), 23.9 (q), 24.8 (t), 26.1 (d), 263 (t), 32.6 (t), 37.3 (s), 48.9 (d), 60.7 (q), 111.8 (s), 124.3 (s), 131.0 (s), 131.1 (s), 139.3 (s), 148.8 (s), 150.8 (s), 150.9 (s), 174.2 (s).
EI-MS m/z (relative intensity): 344 [M]+(100), 329 [M-$CH_3$]+(41), 311 (60), 283 (21), 245 (30), 241 (19), 205 (42).
HR-MS m/z: 344.1963 [M]+, $C_{21}H_{28}O_4$ 344.1988 (calculated).

EXAMPLE 6

63 Milligrams of the 3,4,4a,5,8,9,10,10a-octahydro-1,4a-dimethyl-7-(1-methylethyl)-5,8-dioxo-2-phenanthrenecarboxylic acid obtained in Example 1 was dissolved in 8 ml of ether, then under ice-cooling condition, a diazomethane-ether solution was added thereto and the mixture was stirred for 30 minutes. Ether was removed by distillation. The resulting crude product was purified by a silica gel column chromatography (eluant: ether/n-hexane=⅓) to obtain 8.8 mg of methyl 3,4,4a, 5,8,9,10,10a-octahydro-1,4a-dimethyl-7-(1-methylethyl)-5,8-dioxo-2-phenanthrenecarboxylate.

$^1H$ NMR 270 MHz, chloroform-$d_1$) δppm: 1.10 (3H, d, J=6.8 Hz), 1.11 (3H, d, J=6.8 Hz), 1.17 (3H, s), 1.35–1.56 (2H, m), 2.00 (3H, d, J=1.3 Hz), 2.15–2.55 (5H, m), 2.71–2.83 (2H, m), 3.00 (1H, sept d, J=6.8, 1.1 Hz), 3.73 (3H, s), 6.36 (1H, d, J=1.1 Hz).

EXAMPLE 7

A mixture consisting of 60 mg of the 5,6,8,8a,9,10-hexahydro-8-hydroxymethyl-4b,8-dimethyl-2-(1-methylethyl)-1,4,7(4bH)-phenanthrenetrione obtained in Example 2, 0.1 ml of acetic anhydride and 1 ml of pyridine was stirred at room temperature for 2.5 hours. The reaction mixture was poured into ice water, and extracted with ether. The organic layer was washed with an aqueous saturated with sodium chloride, dried with anhydrous magnesium sulfate, and concentrated. The resulting crude product was purified by a silica gel column chromatography (eluant: ether/n-hexane=⅓) to obtain 41 mg of 8-(acetoxymethyl)-5,6,8,8a,9,10-hexahydro-4b,8-dimethyl-2-(1-methylethyl)-1,4,7(4bH)-phenanthrenetrione.

$^1H$ NMR (270 MHz, chloroform-$d_1$) δppm: 1.07 (3H, d, J=7.0 Hz), 1.08 (3H, d, J=7.0 Hz), 1.41 (3H, s), 1.20 (3H, s), 1.77 (1H, dd, J=12.7, 1.5 Hz), 1.88–2.03 (1H, m), 2.00 (3H, s), 2.31 (1H, ddd, J=20.3, 11.3, 7.0 Hz), 2.48 (1H, ddd, J=16.0, 6.6, 3.7 Hz), 2.70–2.85 (2H, m), 2.91–3.08 (2H, m), 4.05 (1H, d, J=11.5 Hz), 4.53 (1H, d, J=11.5 Hz), 6.35 (1H, d, J=1.1 Hz).

EXAMPLE 8

A mixture consisting of 37 mg of the 1,2,3,4,a,5,8,9,10,10a-decahydro-2-hydroxy-1-(hydroxymethyl)-1,4a-dimethyl-7-(1-methylethyl)-5,8-dioxo-phenanthrene obtained in Example 3, 0.1 ml of acetic anhydride and 0.5 ml of pyridine was stirred at room temperature for 15 hours. The reaction mixture was poured into ice water, and extracted with ether. The organic layer was washed with an aqueous solution saturated with sodium chloride, dried with anhydrous magnesium sulfate, and concentrated. The resulting crude product was purified by a silica gel column chromatography (eluant: ether/n-hexane =⅓) to obtain 27 mg of 2-(acetyloxy)-1-(acetoxymethyl)-1,2,3,4,4a,5,8,9,10,10a-decahydro-1,4a-dimethyl-7-(1-methylethyl)-5,8-dioxo-phenanthrene.

$^1H$ NMR (270 MHz, chloroform-$d_1$) δppm: 1.88 (2H, m), 2.01–2.11 (1H, m), 2.07 (3H, s), 2.05 (3H, s), 2.26 (1H, ddd, J=20.1, 11.8, 7.0 Hz), 2.70–2.88 (2H, m), 3.00 (1H, sept d, J=7.0, 1.1 Hz), 4.26 (1H, d, J=12.0 Hz), 4.33 (1H, d, J=12.0 Hz), 4.57–4.55 (1H, m), 6.35 (1H, d, J=1.1 Hz).

EXAMPLE 9

150 Milligrams of 3,4,4a,5,8,9,10,10a-octahydro-1,4a-dimethyl-7-(1-methylethyl)-5,8-dioxo-2-phenanthrenecarboxylic acid was dissolved in 10 ml of ethyl acetate. Thereto was added, as a catalyst, 3 ml of an ethyl acetate suspension containing 15 mg of 10% palladium-carbon. The container inside was purged with hydrogen gas, and the contents were stirred at room temperature for 3 hours. The catalyst was removed by filtration, and the filtrate was concentrated under reduced pressure to obtain 135 mg of 3,4,4a,9,10,10a-hexahydro-5,8-dihydroxy-1,4a-dimethyl-7-(1-methylethyl)-2-phenanthrenecarboxylic acid.

$^1$H NMR (270 MHz, chloroform-d$_1$) δppm: 1.20 (3H, s), 1.23 (6H, d, J=6.8 Hz), 1.55-1.76 (2H, m), 2.17 (3H, d, J=1.1 Hz), 2.21-2.51 (3H, m), 2.53-2.70 (2H, m), 2.88 (1H, dd, J=6.7, 4.3 Hz), 3.03-3.11 (1H, m), 3.07 (1H, sept, J=6.8 Hz), 6.41 (1H, s).

EXAMPLE 10

600 Milligrams of 3,4,4a,5,8,9,10,10a-octahydro-1,4a-dimethyl-7-(1-methylethyl)-5,8-dioxo-2-phenanthrenecarboxylic acid was dissolved in 25 ml of tetrahydrofuran. Thereto was added 50 ml of an aqueous solution prepared by dissolving 6 g of sodium hydrosulfite and the mixture was stirred at room temperature for 30 minutes. To the reaction mixture was added with water, and the mixture was extracted with ethyl acetate. The organic layer was washed with an aqueous solution saturated with sodium chloride, dried with anhydrous magnesium sulfate, and concentrated. To the concentrate were added 6 ml of pyridine and 0.6 ml of acetic anhydride, and the mixture was stirred at room temperature for 17 hours. The reaction mixture was poured into ice water, and the mixture was extracted with ethyl acetate. The organic layer was washed with an aqueous solution saturated with sodium chloride, dried with anhydrous magnesium sulfate, and concentrated. The resulting crude product was fractionated and purified by a silica gel column chromatography (eluant: chloroform/methanol=50:1) to obtain 150 mg of 3,4,4a,9,10,10a-hexahydro-5,8-diacetyloxy-1,4a-dimethyl-7-(1-methylethyl)-2-phenanthrenecarboxylic acid (diacetyl form) and 180 mg of 3,4,4a,9,10,10a-hexahydro-5-acetyloxy-8-hydroxy-1,4a-dimethyl-7-(1-methylethyl)-2-phenanthrenecarboxylic acid (monoacetyl form).

$^1$H NMR (270 MHz, chloroform-d$_1$) δppm: Diacetyl form: 6.78 (1H, S), 2.75-2.95 (1H, m), 2.31-2.73 (6H, m), 2.35 (3H, S), 2.33 (3H, S), 2.15-2.26 (1H, m), 2.16 (3H, S), 1.53-1.85 (2H, m), 1.18 (3H, d, J=7.0 Hz), 1.15 (3H, d, J=7.0 Hz), 1.10 (3H, S). Monoacetyl form: 6.46 (1H, S), 2.98-3.11 (1H, m), 2.75-2.93 (2H, m), 2.47-2.68 (2H, m), 2.31-2.46 (2H, m), 2.33 (3H, S), 2.13-2.21 (1H, m), 2.15 (3H, S), 1.50-1.71 (2H, m), 1.16 (6H, d, J=7.0 Hz), 1.13 (3H, S).

EXAMPLE 11

800 Milligrams of 3,4,4a,5,8,9,10,10a-octahydro-1,4a-dimethyl-7-(1-methylethyl)-5,8-dioxo-2-phenanthrenecarboxylic acid was dissolved in 30 ml of tetrahydrofuran. Thereto was added 60 ml of an aqueous solution prepared by dissolving 8 g of sodium hydrosulfite, and the mixture was stirred at room temperature for 30 minutes. The reaction mixture was mixed with water, and the mixture was extracted with ethyl acetate. The organic layer was washed with an aqueous solution saturated with sodium chloride, dried with anhydrous magnesium sulfate, and concentrated. The concentrate was dissolved in 3 ml of dimethyl formamide. Thereto were added 1.2 ml of dimethyl sulfate and 0.7 ml of an aqueous solution prepared by dissolving 930 mg of NaOH, at room temperature, and the mixture was stirred for 30 minutes. The reaction mixture was made acidic by adding 1N hydrochloric acid thereto, and the mixture was extracted with ethyl acetate. The organic layer was washed with an aqueous solution saturated with NaHCO$_3$ and an aqueous solution saturated with sodium chloride, in this order, then dried with anhydrous magnesium sulfate, and concentrated. The resulting crude product was purified by a silica gel chromatography (eluant: ether:n-hexane=1:10) to obtain 720 mg of methyl 3,4,4a,9,10,10a-hexahydro-5,8-dimethoxy-1,4a-dimethyl-7-(1-methylethyl)-2-phenanthrenecarboxylate.

$^1$H NMR (270 MHz, chloroform-d$_1$) δppm: 6.60 (1H, S), 3.80 (3H, S), 3.75 (3H, S), 3.68 (3H, S), 3.30 (1H, sept. J=6.8 Hz), 3.01-3.13 (1H, m), 2.97 (1H, ddd, J=13.3, 7.1, 3.3 Hz), 2.45-2.73 (2H, m), 2.27-2.41 (2H, m), 2.11-2.23 (1H, m), 2.05 (3H, q-like, J=1.3 Hz), 1.48-1.65 (2H, m), 1.23 (3H, d, J=6.8 Hz), 1.21 (3H, d, J=6.8 Hz), 1.15 (3H, S).

EXAMPLE 12

The fraction (4-4) obtained in the above Example was concentrated under reduced pressure. 19 Grams of the resulting residue was subjected to silica gel column chromatography (1,700 g of Merck Silica Gel 60, having 70-230 meshes, a product of Merck), and eluted with 3 liters of 20% ethyl acetate/n-hexane (v/v) and ethyl acetate-n-hexane mixtures of gradually increasing ethyl acetate contents, to obtain fractions (4-4-1 to 4-4-11). Of these fractions, the fraction (4-4-3) was concentrated under reduced pressure to obtain 4.0 g of a residue. The residue was subjected to fractionation and elution by using 1,500 ml of Sephadex LH-20 (a product of Pharmacia); and eluted with a 4 liters of 10% chloroform/methanol (v/v) to obtain fractions (4-4-3-1 to 4-4-3-8). The fraction (4-4-3-4) was concentrated under reduced pressure to obtain 0.41 g of a residue. The residue was recrystallized from methanol to obtain 0.360 g of 1,2,3,4,4a,5,8,9,10,10a-decahydro-1,4a-dimethyl-7-(1-methylethyl)-5,8-dioxo-1-phenanthrenealdehyde as light yellow platy crystals.

Molecular formula: C$_{20}$H$_{26}$O$_3$ (Mw: 314).

[α]$_D^{25}$= +20.3° (c=1.0, methanol).

Rf$_1$: 0.78 [5% methanol/chloroform (v/v)].

Rf$_2$: 0.64 [40% ethyl acetate/n-hexane (v/v)].

IRν$_{max}$ (KBr) cm$^{-1}$: 2970, 1710, 1650, 1600, 1297, 1231, 980, 915, 754.

UVλ$_{max}$ (MeOH) nm: 260 (ε=14570).

$^1$H NMR (400 MHz, chloroform-d$_1$) δppm: 1.09 (3H, S), 1.10 (3H, d, J=6.8), 1.11 (3H, d, J=6.8), 1.16 (3H, S), 0.97-1.13 (1H, m), 1.03-1.18 (1H, m), 1.45 (1H, dd, J=13.2, 1.5), 1.57 (1H, brd, J=14.7), 1.68-1.80 (2H, m), 2.19-2.25 (2H, m), 2.34 (1H, ddd, J=20.0, 11.7, 6.81), 2.72 (1H, brd, J=13.2), 2.80 (1H, ddd, J=19.0, 5.4, 1.0), 2.99 (1H, sept, J=6.8, 1.0), 6.34 (1H, J=1.0), 9.77 (1H, d, J=1.0).

$^{13}$C NMR (100 MHz, Chloroform-d$_1$) δppm: 17.3 (t), 18.8 (t), 19.3 (g), 21.3 (g), 21.4 (g), 24.3 (g), 26.2 (t), 26.4 (d), 34.0 (t), 35.8 (t), 38.6 (s), 48.4 (s), 52.8 (d), 132.0 (d), 142.6 (s), 149,1 (s), 153.0 (s), 187.6 (s), 187.7 (s), 204.7 (s).

EXAMPLE 13

The fraction (7) obtained in the above Example was concentrated under reduced pressure. Of 200 g of the residue obtained, 30 g was subjected to silica gel column chromatography (300 g of Merck Silica Gel 60, 70-230 meshes, a product of Merck), then eluted with 4 liters of 5% methanol/chloroform (v/v) to obtain fractions (7-1 to 7-13). The fraction (7-7) was concentrated under reduced pressure to obtain 0.72 g of a residue. The residue was subjected to fractionation and elution by using 300 ml of Sephadex LH-20 (a product of Pharmacia), and with 1 liter of methanol to obtain fractions (7-7-1 to 7-7-7). The fraction (7-7-3) was concentrated under reduced pressure to obtain 0.184 g of a residue. The residue was subjected to fractionation and elution by using high performance liquid chromatography (YMC PACKED COLUMN 343 I-15 ODS 20×250 mm, a product of Yamamura Kagaku Kenkyusho K.K.), and subjected to fractionation and elution with 300 ml of methanol to obtain fractions (7-7-3-1 to 7-7-3-3). The fraction (7-7-3-2) was concentrated under reduced pressure to obtain 0.03 g of a residue. The residue was subjected to fractionation and elution by using high performance liquid chromatography (TSK-GEL Silica-60 20×250 mm, a product of Tosoh Corporation), and with 100 ml of 5% methanol/chloroform (v/v) to obtain fractions (7-7-3-2-1 to 7-7-3-2-3). The fraction (7-7-3-2-3) was concentrated under reduced pressure to obtain 10 mg of 1,2,3,4,4a,5,8,9,10,10a-decahydro-1,4a-dimethyl-3-hydroxy-7-(1-methylethyl)-5,8-dioxo-1-phenanthrenecarboxylic acid as an amorphous substance.

Molecular formula: $C_{20}H_{26}O_5$ (Mw: 346).

$[\alpha]_D^{25} = +35.0°$ (c=0.06, chloroform).
$Rf_1$: 0.15 [5% methanol/chloroform (v/v)].
$Rf_2$: 0.04 [40% ethyl acetate/n-hexane (v/v)].
$IR\nu_{max}$ (KBr) $cm^{-1}$: 3430, 2960, 1700, 1650, 1470, 1380, 1230, 1030, 910, 760.
$^1H$ NMR (400 MHz, $C_5D_5N$) $\delta$ ppm: 1.04 (3H, d, J=6.8), 1.06 (3H, d, J=6.8) 1.20–1.60 (3H, m), 1.50 (3H, S), 1.66 (3H, S), 2.05-2.16 (1H, m), 2.32 (1H, dd, J=19.5, 6.8), 2.38 (1H, dd, J=10.7, 4.4), 2.87 (1H, dd, J=19.0, 4.9), 3.03 (1H, sept, J=6.8), 3.16 (1H, dd, J=12.4, 2.9), 3.68 (1H, dd, J=13.7, 4.4) 4.98 (1H, tt, J=11.2, 4.4), 6.47 (1H, S).
$^{13}C$ NMR (67.5 MHz, chloroform-$d_1$) $\delta$ ppm: 18.9 (g), 19.0 (t), 21, 4×2 (g), 26.4 (d), 26.6 (t), 28.7 (g), 39.9 (s), 44.1 (s), 44.9 (t), 45.7 (t), 52.6 (d), 64.4 (d), 132.1 (d), 143.2 (s), 148.1 (s), 153.2 (s), 181.9 (s), 187.8×2 (s).
EI-MS m/z (relative intensity): 346 [M]+ (20), 328 [M-H2O]+(100), 313 (50), 300 (48), 282 (87), 267 (67), 189 (33), 128 (37), 91 (53).

The results of pharmacological tests for compounds of the present invention are shown below.
1. Test on inhibition for interleukin-1 (IL-1) released from human peripheral mononuclear cells A healthy human peripheral blood was sampled, and mononuclear cells were collected from the blood by using Ficoll-Paque® (manufactured by Pharmacia LKB Biotechnology Incorporated). The mononuclear cells were suspended in a RPMI-1640 medium (manufactured by Nissui Seiyaku Co., Ltd.) containing 100 units/ml of penicillin, 0.1 µg/ml of streptomycin and 10% of fetal calf serum, so that the cell count became 2×10⁶ per ml. To one volume of the suspension was added one volume of a test compound solution ($3\times10^{-6}$ g/ml). There was further added one volume of a RPMI medium containing 10 µg/ml of a lipopolysaccharide (LPS). The resulting mixture was cultured in a humidified $CO_2$ incubator containing 5% $CO_2$, at 37° C. for 24 hours. The supernatant liquid of the culture solution was recovered by centrifugation.

The measurement of human IL-1α and human IL-1β released from cells by the stimulus of LPS was conducted by enzymatic immunological assay (EIA). That is, a 96-well plate for EIA was coated with a mouse monoclonal antibody to human IL-1α or human IL-1β, after which a blocking treatment was applied. A sample was added to the plate to give rise to a reaction. Then, the plate was washed. Thereafter, a rabbit polyclonal antibody to human IL-1α or human IL-1β was added to give rise to a reaction. The plate is washed. Then, horse radish peroxidase (POD)-conjugated anti-rabbit IgG antibody was added to give rise to a reaction, after which the unbonded POD-conjugated anti-rabbit IgG antibody was removed by washing the plate. A substrate solution (o-phenylenediamine and hydrogen peroxide) was added to give rise to a reaction, after which an absorbance at 492 nm was measured. Inhibition (%) for IL-1 release was calculated according to the following formula:

Inhibition (%) for IL-1 release = $100\times(1-T_{492}\div C_{492})$ $T_{492}$: Absorbance at 492 nm when the supernatant obtained from the culture solution containing a test compound was used as a sample.

$C_{492}$: Absorbance at 492 nm when the supernatant obtained from the culture solution containing a solvent was used as a sample.

The inhibitions for IL-1α and IL-1β releases as measured according to the above procedure were 25% and 49%, respectively, when the compound ($3\times10^{-6}$ g/ml) of the present invention obtained in Example 1 was used as a test compound.

Also, the inhibitions for IL-1α and IL-1β releases were 78% and 94%, respectively, when the compound ($3\times10^{-6}$ g/ml) of the present invention obtained in Example 2 was used as a test compound.

2. Test on adjuvant-induced arthritis in rat

As a test animal, 8.5-week age Wistar-Lewis strain female rats were used. As an adjuvant, there was used a suspension of 0.5 mg of dead *Mycobacterium butyricum* (manufactured by Difco Laboratories, Inc.) in 0.1 ml of liquid paraffin. The rats were sensitized with the adjuvant intracutaneously at the base of the tail. Starting from the day of sensitization, i.e. day (zero), the paw edema appearing in hind-limbs was measured plethysmographically, by using a foot volume meter (MK-500, manufactured by Muromachi Kiki Co., Ltd.).

A test sample was prepared by suspending a test compound in a 5% gum arabic solution, and orally administered to rats 5 times per week starting from the day of adjuvant sensitization.

As a result, a significant inhibitory activity for arthritis was confirmed in the rat group to which the compound of the present invention obtained in Example 1 had been administered in an amount of 50 mg/kg (Table 1).

TABLE 1

| Group | Groups of adjuvant-induced arthritis | | | Non-sensitized group |
|---|---|---|---|---|
| | Control group | Present compound | | |
| | | 10 mg/kg | 50 mg/kg P.O. | |
| Mean foot Volume | 2.57 ± 0.09 (6) | 2.43 ± 0.07 (6) | 2.18 ± 0.07** (6) | 1.36 ± 0.02 (6) |

In Table 1, each numerical figure indicates the average foot volume (ml) of left and right hind-limbs with a standard error on day 16. Each numerical figure in parenthesis indicates the number of test animals used in each group. Symbol ** indicates a significant difference (P<0.01) in Tukey's multi group comparison test.

What is claimed is:

1. A phenanthrene derivative selected from the group consisting of compounds represented by the general formula (1),

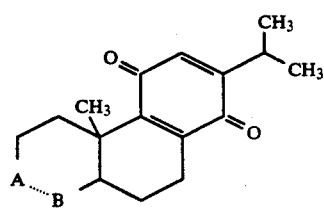
(1)

wherein the group of the formula

is a group of the formula

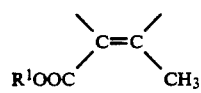

wherein $R^1$ is a hydrogen atom or a lower alkyl group, a group of the formula

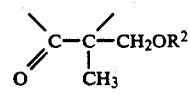

wherein $R^2$ is a hydrogen atom or a lower alkanoyl group, a group of the formula

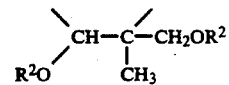

wherein $R^2$ is the same as defined above, a group of the formula

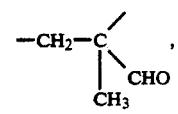

a compound of the formula (2),

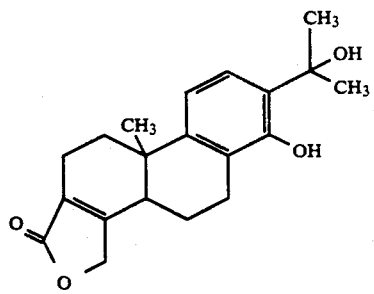
(2)

a compound of the formula (3),

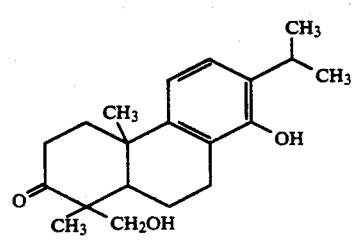
(3)

compounds represented by the general formula (4),

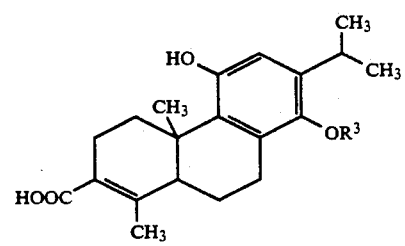
(4)

wherein $R^3$ is a hydrogen atom or a methyl group, a compound of the general formula (7),

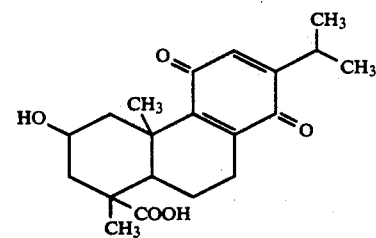
(7)

compounds represented by the general formula (8),

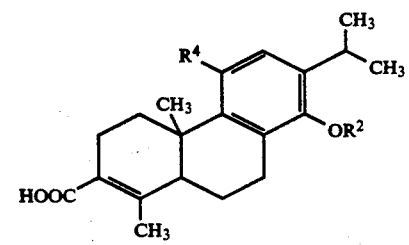
(8)

wherein $R^2$ is the same as defined above and $R^4$ is a lower alkanoyloxy group, or compounds represented by the general formula (9),

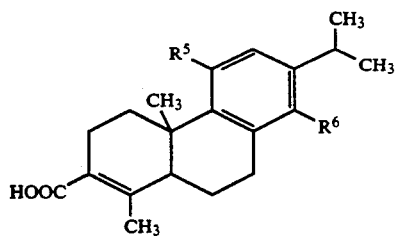

wherein $R^5$ and $R^6$ are each a lower alkoxy group, or a salt thereof.

2. A phenanthrene derivative or a salt thereof according to claim 1, wherein in the general formula (1), the group of the formula —A . . . B— is a group of the formula

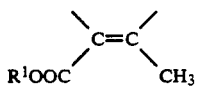

wherein $R^1$ is the same as defined above.

3. A phenanthrene derivative or a salt thereof according to claim 1, wherein in the general formula (1), the group of the formula —A . . . B— is a group of the formula

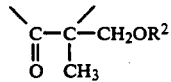

wherein $R^2$ is the same as defined above).

4. A phenanthrene derivative or a salt thereof according to claim 1, wherein in the general formula (1), the group of the formula —A . . . B— is a group of the formula

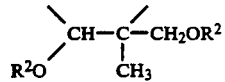

(wherein $R^2$ is the same as defined above) or a group of the formula

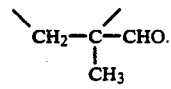

5. A phenanthrene derivative selected from the group consisting of a compound of the formula (2),

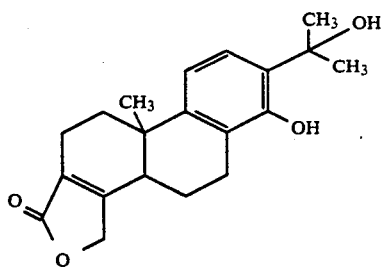

a compound of the formula (3),

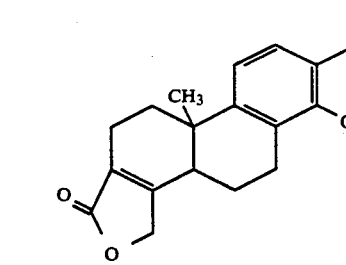

compounds represented by the general formula (4),

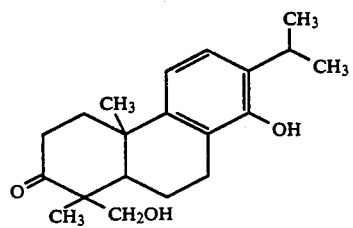

wherein $R^3$ is the same as defined above a compound of the formula (7),

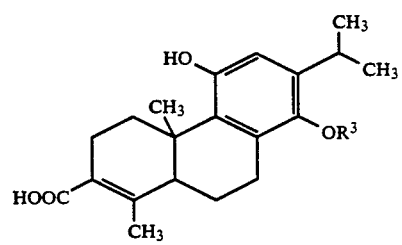

compounds represented by the general formula (8),

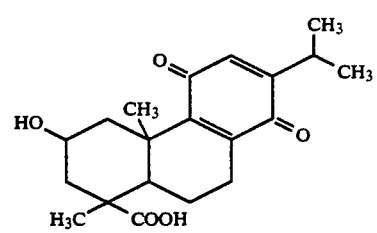

wherein $R^2$ and $R^4$ are each the same as defined in claim 1, and compounds represented by the general formula (9),

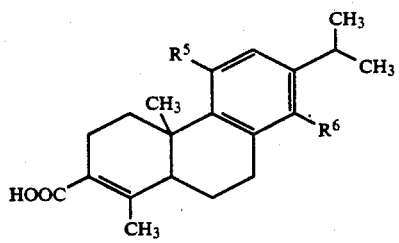

(9)

wherein $R^5$ and $R^6$ are each the same as defined in claim 1 or a salt thereof.

6. 3,4,4a,5,8,9,10,10a-Ocathydro-1,4-a-dimethyl-7-(1-methylethyl)-5,8-dioxo-2-phenanthrenecarboxylic acid.

7. 5,6,8,8a,9,10-Hexahydro-8-hydroxymethyl-4b,8-dimethyl-2-(1-methylethyl)-1,4,7(4bH)-phenanthrenetrione.

8. An interleukin-1 (IL-1) inhibitor containing, as active ingredient(s), phenanthrene derivative(s) selected from the group consisting of compounds represented by the general formulas (1), (4), (8) and (9) and the formulas (2), (3) and (7) as defined in claim 1 or salt(s) thereof.

* * * * *

UNITED STATES PATENT AND TRADEMARK OFFICE
CERTIFICATE OF CORRECTION

PATENT NO. : 5,192,817
DATED : March 9, 1993
INVENTOR(S) : Yoshihisa Takaishi et al.

It is certified that error appears in the above-identified patent and that said Letters Patent is hereby corrected as shown below:

Claim 5, column 24, line 39, delete "above" and insert therefor --in claim 1,--; and Claim 6, column 26, line 3, "4-a-dimethyl-7-(1-" should read --4a-dimethyl-7-(1- --.

Signed and Sealed this

Twenty-fifth Day of January, 1994

Attest:

BRUCE LEHMAN

Attesting Officer

Commissioner of Patents and Trademarks